United States Patent [19]

Clodman et al.

[11] Patent Number: 5,498,603
[45] Date of Patent: Mar. 12, 1996

[54] METHOD FOR THE STIMULATION OF HAIR GROWTH

[76] Inventors: Percy B. Clodman, 209 Searle Ave., Downsview, Ontario, Canada, M3H 4B6; Ossie Clodman, 65 Sunnycrest Rd., Willowdale, Ontario, Canada, M2R 1V4

[21] Appl. No.: 170,772

[22] Filed: Dec. 21, 1993

Related U.S. Application Data

[63] Continuation-in-part of Ser. No. 86,994, Jul. 7, 1993, Pat. No. 5,420,114.

[51] Int. Cl.$^6$ .................................. A61K 7/06
[52] U.S. Cl. .................. 514/25; 514/59; 514/880; 424/195.1
[58] Field of Search .......... 424/195.1; 514/23, 514/25, 53, 54, 59, 858–865, 880, 887

[56] References Cited

U.S. PATENT DOCUMENTS

| | | | |
|---|---|---|---|
| 3,525,340 | 8/1970 | Gilbert | 606/221 |
| 3,777,016 | 12/1973 | Gilbert | 514/23 |
| 4,395,398 | 7/1983 | Yamamoto | 424/642 |
| 4,466,961 | 8/1984 | Szijjártó et al. | 514/23 |
| 4,503,037 | 3/1985 | Szijjarto et al. | 424/94.4 |
| 4,900,550 | 2/1990 | Lowry | 424/195.1 |
| 5,181,914 | 1/1993 | Zook | 604/307 |
| 5,264,206 | 11/1993 | Bohn et al. | 424/61 |

Primary Examiner—Douglas W. Robinson
Assistant Examiner—Kathleen Kahler Fonda
Attorney, Agent, or Firm—Cushman Darby & Cushman

[57] ABSTRACT

A dermatological pharmaceutical composition for stimulating hair growth and for the treatment of conditions of the skin selected from the group consisting of (a) benign moles, papillomas and seborrheic keratoses;
(b) unsightly freckles, pimples and blemishes;
(c) stasis dermatitis;
(d) dermal ulcers; and
(e) fungal nail infections; and
(f) gingival and mucous membrane inflammations;

the composition comprising an effective amount of tannic acid, a debriding agent and a pharmaceutically acceptable carrier therefore.

1 Claim, No Drawings

METHOD FOR THE STIMULATION OF HAIR GROWTH

RELATED APPLICATIONS

This is a continuation-in-part application of Ser. No. 08/086,994, filed Jul. 7, 1993, now U.S. Pat. No. 5,420,114.

FIELD OF THE INVENTION

This invention relates to dermatological compositions suitable for the treatment of unsightly skin conditions such as benign moles and soft papillomas, skin disorders or abnormalities such as ulcers, stasis dermatitis and gingival and mucous membrane inflammations; and to methods for the removal or treatment thereof.

BACKGROUND OF THE INVENTION

U.S. Pat. No. 3,525,340- Gilbert, J. G., issued Aug. 25, 1970 discloses a surgical dressing having coating compositions comprising a pharmacologically active solution of tannic, acid, cinnamic acid and polyvinyl pyrolidone for the control of bleeding of a wound and broad spectrum anti-bacterial activity. The adhesive and stability properties of the compositions provide improved utility.

U.S. Pat. No. 3,777,016- Gilbert, J. G., issued Dec. 4, 1973, describes pharmaceutical compositions comprising tannic acid, cinnamic alcohol and polypyrolidone and a method for aiding the reparation of damaged skin and subcutaneous tissue by topical treatment. The cinnamic alcohol is present to solubilize bacterial and fungal organic material and skin and subcutaneous tissue which have been abraded, incised or lacerated. The tannic acid, on the other hand, is present to precipitate such entities and also as an astringent.

U.S. Pat. No. 4,395,398- Yamamoto, H., issued Jul. 26, 1983, describes use of tannic acid inter alia as an astringent in a dental haemostatic composition for local application to small hemorrhage in the dental area. An essential feature of the composition is a surfactant which provides enhanced coagulation of the blood.

U.S. Pat. No. 4,503,037- Szijjarto et al, issued Mar. 5, 1985 describes compositions comprising tannic acid, inter alia, a carbohydrate, an anthocyan and/or flavonone and/or pectin, plant wax, volatile oil and a $C_2$–$C_4$ alkanol for the treatment and post-treatment of surface wounds of the skin, especially burns, herpes processes caused by virus, pyogenic processes of the skin, keloid and hypertrophic scar tissue, surgical wounds, post-treatment of frozen skin surface and to induce epithelization in case of wounds caused by abrasions or by caustic materials. The above listed components are stated to be essential to the composition to ensure disinfection of the surface of the wound and to increase epithelization and, thus, relieve pain.

It is known that tannic acid, 6% W/W is the active ingredient of a commercial preparation sold for the treatment of cold sores, fever blisters, and canker sores. It is thus sold for the express purpose of treating herpes processes caused by a virus.

None of the prior art known to applicants describes the use of pharmaceutical compositions comprising tannic acid as hereinafter described for the treatment of unsightly skin conditions, abnormalities and gingival and mucous membrane inflammation as hereinafter defined.

SUMMARY OF THE INVENTION

It is an object of the present invention to provide pharmaceutical compositions for the non-surgical removal of benign moles, papillomas and seborrheic keratoses; freckles, pimples and unsightly blemishes.

It is a further object of the present invention to provide synergistic pharmaceutical compositions for the treatment of finger and toe nail fungal infections.

It is a yet further object of the invention to provide pharmaceutical compositions for the treatment of stasis dermatitis.

It is a still yet further object of the present invention to provide pharmaceutical compositions for the treatment of dermal leg ulcers.

It is a further object of the present invention to provide dermatologic compositions for the stimulation of mammalian hair growth.

It is a yet further object of the present invention to provide pharmaceutical compositions for the treatment of gingival and mucous membrane inflammations.

It is a still further object of the present invention to provide methods for the removal or treatment of skin conditions as hereinabove described.

These and other objects of the present invention will be readily apparent from a reading of the specification as a whole.

Accordingly, in one aspect the invention provides dermatological pharmaceutical compositions for the treatment of conditions of the skin selected from the group consisting of (a) benign moles, papillomas and seborrheic keratoses;

(b) unsightly freckles, pimples and blemishes;

(c) stasis dermatitis;

(d) dermal ulcers;

(e) fungal nail infections;

(f) gingival and mucous membrane inflammations; and for stimulating hair growth;

said compositions comprising an effective amount of tannic acid, a debriding agent and a pharmaceutically acceptable carrier therefore.

In the treatment of fungal nail infections the composition further comprises an effective synergistic amount of antifungal topical agent. Example of a preferred antifungal topical agent fungicide is Tolnaftate (TINACTIN™ cream; O-2-naphthyl m, N-dimethyl thiocarbanilate); and of an antifungal fungistat is Miconazole (common name).

Preferably, the debriding agent is a carbohydrate, preferably a pentose or hexose carbohydrate, such as for example, glucose, lactose, fructose or mannose; sucrose and dextrose.

It is known that aloe vera gel, obtained from exudates of the Aloe Vera plant (*Aloe barbadensis* Miller) a member of the lily family (Liliaceae) has been used in cosmetics as a skin moisturizer, as a food additive and in pharmaceutical preparations, as burn creams, sprays and suntan lotions. It is claimed to improve the skin condition and demonstrate restorative effects. Aloe vera is typically obtained as a powder by concentration by a factor, for example, of about 200 of aloe vera gel obtained from the leaf of the plant. The gel is typically obtained as a semi-solid "fillet" which contains more than 200 different substances before processing, chiefly polysaccharides, glycoproteins, vitamins, minerals and enzymes.

We have found that the beneficial effects of the compositions as hereinabove defined are enhanced when further comprising aloe vera.

Accordingly, in a preferred aspect the invention provides pharmaceutical compositions as hereinabove defined further comprising aloe vera.

The aloe vera is present in a suitable and effective amount, typically 0.1%–5% W/V, preferably, 0.5%–1% W/V and more preferably 0.75% W/V.

We have found that compositions in the form of liquids or ointments, creams, powders and the like suitably formulated with pharmaceutically acceptable diluents and carriers for the active ingredients are effective for the useful purposes as hereinabove defined.

The dermatological compositions of the present invention in the form of a liquid formulation are prepared by dissolving the ingredients in water and/or water miscible solvents, such as mono or polyhydroxyl compounds. The compositions can be prepared according to conventional methods such as mixing, dissolving or dispersing the appropriate ingredients. Preferably, the compositions further comprise other biogically-active ingredients. For example, bacteriostats and/or fungiostats and/or antioxidants. Preferred bacteriostats and preservatives are esters of p-hydroxybenzoic acids such as methyl, butyl, m- or p-hydroxybenzoic acids.

Suitable amounts of tannic acid ranging from 0.1%–5.0% W/V, preferably 1–3% W/V, and a carbohydrate, 10%–30% W/V, preferably 12%–18% W/V, provide satisfactory results.

In a further aspect the invention provides a method for the treatment of non-viral skin defects defined hereinabove comprising applying to a benign growth, papilloma, seborrheic keratosis, fungal-infected nail, ulcer, unsightly or infected skin and scalp, a pharmaceutically acceptable and effective amount of a composition as defined hereinabove. Thus, the compositions according to the invention are applied on the surface of the unsightly growth or skin, on the skin ulcer or fungal infected nail, including adjacent tissue, or on the bald or balding area of the head as required by the person. The above treatments are repeated over a suitable period of time as may be required.

To our knowledge, there is no known antifungal topical medication that is effective per se against fungal infection of nails. We have found that compositions according to the invention synergize fungicidal action of a topically applied antifungal agent. Typically, a nail fungus infection often follows an injury to the nail-bed area, such as that caused by a falling object, stubbing of the toe, by other accident, or by prolonged concentrated pressure e.g. from poorly fitting footwear. This results in a localized development of internal necrotic collagen or scar-like tissue, which typically blocks adequate penetration by medication. The topical application of compositions according to the invention provides synergistic antifungal activity resulting in growth of healthy nail tissue.

In order that the invention may be better understood preferred embodiments will now be described by way of example only.

EXAMPLE 1

The following liquid composition was prepared for the treatment of the scalp to promote hair growth:

|  | % W/V |
|---|---|
| Tannic acid | 1.10 |
| Aloe-A Powder (1:200)* | 0.75 |
| Dextrose (anhydrous) | 16.70 |
| m-paraben | 0.10 |
| p-paraben | 0.05 |
| Isopropyl alcohol | 5.00 |
| vitamin-E oil (1,000 U/ml) | 1.00 |
| Octyl dimethyl PABA | 2.00 |
| Tween 80 | 2.00 |
| Jajoba | 2.00 |
| Glycerin | 24.00 |
| Propylene Glycol | 33.30 |
| Water | 12.00 |
|  | 100.00 |

*Aloe-A Pdr (1–200) is Aloe Vera Gel concentrated by a factor of 200. Therefore the final product has a concentration of active ingredient equal to 150% of that of Aloe Vera Gel. The powder was obtained from a commercial source, namely, Chemetics Laboratories, Inc., Dallas, Texas.

The composition can be prepared as follows:

1. Measure off total amount of Glycerin required.
2. Dissolve Aloe-A pdr in Alcohol.
3. Dissolve Tannic Acid in Glycerin q.s.
4. Dissolve Parabens together in Alcohol q.s.
5. Dissolve Dextrose 12% ONLY in Dist. Water 12%. Heat gently p.r.n.
6. Dissolve Dextrose 4.7% in Glycerin q.s. Combine both dextrose solutions.
7. Combine PABA, Tween-80, and Jajoba in a large mortar and triturate to a smooth mixture.
8. Add the following components in order, incorporating each in the emulsion: Vitamin E Oil, Parabens solution, Tannic Acid Solution, Aloe-A solution, Isopropyl Alcohol (which may be used to wash out residual Tannic Acid and Aloe-A), Dextrose Solution, remainder of Glycerin.
9. Transfer entire contents to an amber glass bottle.
10. Add the Propylene Glycol and shake well.

EXAMPLE 2

The following ointment composition was prepared:

|  | % W/W |
|---|---|
| Tannic Acid | 2.10 |
| Dextrose Anhydrous | 12.50 |
| Liquid Glucose (Corn syrup) | 10.00 |
| Aloe-A Pdr (1–200) | 0.75 |
| m-Paraben | 0.10 |
| p-Paraben | 0.05 |
| Cetyl Alcohol | 2.00 |
| Isopropyl Alcohol 99% | 3.00 |
| Vitamin-E Oil (1000 U/ml) | 3.00 |
| Demineralized Water | 7.50 |
| Hydrophilic Petrolatum USP | 44.00 |
| Wool Alcohols Ointment (Eucerin) | 5.00 |
| Glycerin | 10.00 |
|  | 100.00 |

The composition can be prepared as follows:

1. Dissolve dextrose 7.5% in water 7.5%. Dissolve dextrose 5% in glycerin 10%. Gently heat each solution prn to dissolve.
2. Liquefy cetyl alcohol over water bath. (Do not overheat)
3. Add Vit. E Oil to the melt.

4. Weigh out total amount of hydrophilic pet. and place in a warm mortar. Add about 5% of it (or more, according to available space) to the melt.

5. Add all of Eucerin to the melt.

6. Add total melted mixture to hydrophilic pet. in the warm mortar and mix.

7. Add the 2 dextrose solutions (in turn) to mixture (in mortar) and emulsify.

8. Dissolve tannic acid in alcohol 2% and add to mixture.

9. Dissolve parabens in alcohol 1% and add to mixture.

10. Dissolve aloe in glycerin about 2% and add.

11. Slowly add liquid glucose and emulsify.

EXAMPLE 3

The following liquid composition was prepared:

|  | % W/V |
| --- | --- |
| Dextrose Anhydrous | 10.00 |
| Liquid Glucose (Corn Syrup) | 15.00 |
| Tannic Acid | 2.00 |
| Aloe-A Pdr (1–200)* | 0.75 |
| m-Paraben | 0.10 |
| p-Paraben | 0.05 |
| Isopropyl Alcohol 99% | 2.00 |
| Zinc sulphate | 0.10 |
| Glycerin | 42.00 |
| Propylene Glycol | 20.00 |
| Distilled Water | 8.00 |
|  | 100.00 |

The composition can be made as follows:

1. Measure off total volume of Glycerin required.
2. Dissolve Aloe-A pdr in Glycerin q.s.
3. Dissolve Tannic Acid in Glycerin q.s. (sol. 1:1)
4. Dissolve Parabens together in Alcohol q.s. (sol. 1:3.5)
5. Dissolve Zinc Sulphate in dist. water 0.1% (sol. 1:1)
6. Dissolve Dextrose 7.5% ONLY in dist. water 7.5%. Heat gently prn.
7. Dissolve Dextrose 2.5% ONLY in Glycerin q.s.
8. Combine all solutions in amber-glass container. Use glycerin or propylene glycol to wash out residual Aloe-A and Tannic Acid.
9. Add remaining (unused) portion of Glycerin. Shake well.
10. Add remaining propylene glycol. Shake well.
11. Add Liquid Glucose in divided amounts, shaking after each addition.

RESULTS

Except where stated, the pharmaceutical composition defined in Example 2 was used as a medical treatment for the following ailments/conditions on a male patient (A), aged 72 years, and a male patient (B), aged 70 years, with the following results. Patient A was an insulin-dependent diabetic who had previously undergone bilateral graft surgery in the groin, which characterizes him as having poor blood circulation often resulting in dermal leg ulcers and stasis dermatitis.

Patient A

1. Soft papilloma—Soft, hanging, underarm growth on left side was treated with one to two applications daily. The tumour disappeared entirely after about one week. A similar growth on the right side shrank in size.

2. Seborrheic keratosis—A brown elevated growth about 1 cm. in diameter, with a rough surface, and located on the inner upper-left thigh, was treated with 2 to 3 applications daily. Over a four-week period, the brown colour and the elevation of the growth gradually receded until only a small crater-like opening, from which a clear viscous fluid was discharging, remained at the center. After continued treatment for 3 to 4 additional weeks, the fluid emission ceased and the opening closed. On the few occasions when applications were missed, regrowth could be observed.

3. Mole—A brown, elevated lesion, of about ¼ inch diameter, on the upper anterior portion of the cheek, and of approximately 50 years duration, was treated with 3 to 4 applications daily, resulting in the gradual recession of the brown colour, shrinkage, and decrease in thickness. After about three months, the mole was gone and the area was completely healed. A second mole about ½ inch distant, undiagnosed but similar in appearance, was also successfully treated at the same time.

On the few occasions when treatment was interrupted, there was no evidence of regrowth, unlike seborrheic keratoses.

4. Infected Mole—An ugly lesion on the chin, of approximately ⅜ inch diameter and elevated about 1/8 inch above the surrounding skin was diagnosed as an infected mole. It was treated with 3 to 4 applications daily, with gradual healing and reduction in size. After about 6 weeks, it remained as a round elevation at least 80% smaller than at the beginning of treatment and was covered with skin of normal appearance.

5. Male Pattern Baldness—The part of the scalp that was treated with the liquid formulation of Example 1 was completely bald except for a slight growth of very fine fuzzy (vellus) hairs. With applications two or three times daily over a few weeks, dark-coloured hairs gradually grew in, eventually up to 5 inches in length. On discontinuation of treatment, the hair gradually shrank and reverted to its original state.

6. Nail Fungus—The right big-toe nail was deeply discoloured a reddish-greenish brown and the inner nail-space was tightly impacted with a whitish powdery material. The nail was treated with 3 to 4 applications daily for 6 to 8 weeks of the ointment composition according to Example 2 in 1:1 W/W% admixture with Tolnaftate USP (TINACTIN™ cream), and led to the separation of the nail into two parts. The upper portion of the nail which peeled off was a layer having an approximate thickness of 0.007 inch, and the lower intact portion had a thickness of about 0.025 inch. This newly-exposed lower portion had an upper surface which was pink in colour. It evidently was a freshly-grown healthy nail which was replacing the previous diseased one. The lower surface of the peeled-off nail revealed traces of the fungal material.

7. Pimples and Blemishes—Various facial pimples and skin blemishes of recent origin were treated from time-to-time with applications 2 to 3 times daily. They would routinely clear up in two to three days.

8. Dermal Leg Ulcers—A crater-like leg ulcer, about 3/16 inch in diameter (almost 5 mm), developed about 6 inches above the left heel. After about three weeks of treatment, the crater closed with a new skin-covering but of distinctly brownish discolouration. With continued treatment of about two more weeks, the discolouration was significantly reduced. The healing time required to close this ulcer was in sharp contrast to that required for an ulcer just above the left heel three years earlier.

This earlier ulcer, which was approximately twice the size of the new one, had healed after conventional treatments over more than a year. These involved a series of wet compresses each followed by application of antibiotic ointment. However the new skin had remained badly discoloured. On being treated further simultaneously with the 1993 leg ulcer, this discolouration was similarly reduced.

9. Stasis Dermatitis—An extremely itchy rash (professionally undiagnosed) on the right leg between the knee and ankle was treated twice daily, with gradual relief from itching. After about three weeks, the rash was completely healed without further symptoms.

Patient B

1. Seborrheic keratosis—A brown elevated growth, with a rough surface and of irregular shape, comprised an area of about 1 sq.cm. and was located on the lower right thigh. It was treated with applications of the above composition varying in frequency from zero to twice daily. After about two to three months, with the brown colour eliminated but with the rough surface remaining, treatment was stopped. The lesion gradually regrew to its original condition. A similar lesion nearby, treated simultaneously but over a longer period, has not regrown.

2. Mole—A dark-brown, round elevated lesion in the upper region of the right cheek-bone, over a number of years had grown to almost 1 cm. in diameter, had acquired a rough edge, and had become virtually black. In June, 1992, it was determined to be benign. Treatment with the above composition, averaged about one application daily. After 7 months of treatment the lesion had shrunk to about half its maximum size and the treatment was stopped for one month. In contrast to the experience with the seborrheic keratoses, there was no retrogressive effect. Treatment was resumed with two to three applications daily which provided a gradual improvement to become less than 0.2 cm. in diameter. The lesion was almost as light as normal skin and has only very slight elevation.

3. Patient B when on continual prosthodontic treatment involving a total of three diagnosed dental root abscesses was treated with the liquid formulation of Example 3. The following observations were recorded.

Severe Gum Inflammation and Pain—On at least three occasions, gum areas adjacent to diagnosed dental root abscesses became inflamed and quite painful. These were treated by the application of compresses of the above formulation. The first was usually kept in place for about 2 hours and resulted in a lessening of the acute pain. If time permitted, a second compress was applied also for about 2 hours and it relieved the pain further. In all instances a final compress, which was applied at bedtime and kept in place overnight, resulted in complete relief from pain.

Remission of Bleeding and Pain on Extraction— The extraction of the root of a rear molar remaining after fracture of the crown of the tooth which had been anchoring a bridge, resulted in an unrelieved bleeding socket accompanied by pain. Application of a compress of the above formulation resulted not only in immediate cessation of bleeding but also relief from pain in a matter of minutes.

Patients C, D, E, F

1. Over a period of time, four patients designated C, D, E and F were treated with the formulation of Example 3 for inflammation of gingival and mucous membrane tissues. Of the four, three patients showed unexpected, distinctly superior responses to what had been achieved with conventional treatment. The fourth patient, whose condition was attributed to a viral infection, did not have a positive response.

It is to be understood that modifications to the preferred embodiments of the invention described and illustrated herein can be made without departing from the scope and spirit of the invention as defined in the appended claims.

We claim:

1. A method of stimulating hair growth on the scalp of a man having male pattern baldness, said method comprising applying to the scalp a pharmaceutically acceptable and effective amount of a composition comprising tannic acid, a debriding agent, and a pharmaceutically acceptable carrier therefore, wherein at least a slight growth of fine hair is present on the scalp at the time of said application.

\* \* \* \* \*